(12) United States Patent
Mairal et al.

(10) Patent No.: US 7,732,173 B2
(45) Date of Patent: Jun. 8, 2010

(54) ETHANOL RECOVERY PROCESS

(75) Inventors: Anurag P. Mairal, Fremont, CA (US); Alvin Ng, Palo Alto, CA (US); Richard W. Baker, Palo Alto, CA (US); Ivy Huang, Palo Alto, CA (US); Jennifer Ly, San Jose, CA (US)

(73) Assignee: Membrane Technology and Research, Inc., Menlo Park, CA (US)

( * ) Notice: Subject to any disclaimer, the term of this patent is extended or adjusted under 35 U.S.C. 154(b) by 846 days.

(21) Appl. No.: 11/494,900

(22) Filed: Jul. 28, 2006

(65) Prior Publication Data

US 2007/0031954 A1 Feb. 8, 2007

Related U.S. Application Data

(60) Provisional application No. 60/705,003, filed on Aug. 3, 2005.

(51) Int. Cl.
*C12P 7/06* (2006.01)

(52) U.S. Cl. ..................................................... 435/161

(58) Field of Classification Search ................... 435/161
See application file for complete search history.

(56) References Cited

U.S. PATENT DOCUMENTS

| 4,305,790 | A | * | 12/1981 | Kramer, Sr. .................. 203/19 |
| 4,326,036 | A | | 4/1982 | Hayes |
| 6,755,975 | B2 | | 6/2004 | Vane et al. |
| 6,899,743 | B2 | | 5/2005 | Wijmans et al. |

* cited by examiner

*Primary Examiner*—Jon P Weber
*Assistant Examiner*—Kailash C Srivastava
(74) *Attorney, Agent, or Firm*—J. Farrant

(57) ABSTRACT

A process for producing and recovering light alcohols, particularly ethanol, alcohol mixtures containing ethanol, and ABE mixtures (alcohol mixtures containing acetone, butanol and ethanol), using a combination of steps including fermentation, first membrane separation, dephlegmation and dehydration by second membrane separation.

39 Claims, 4 Drawing Sheets

ETHANOL RECOVERY PROCESS

This application claims the benefit of U.S. Provisional Application Ser. No. 60/705,003, filed Aug. 3, 2005 and incorporated herein by reference.

BACKGROUND OF THE INVENTION

Ethanol, an alcohol derived primarily from the fermentation of sugars, is a sustainable, low cost and environmentally-friendly energy alternative to fossil fuel. It is compatible with current and future transportation systems and results in near-zero net greenhouse gas emissions. The sugars required for the fermentation process may be obtained from multiple sources, and any substance capable of being treated to yield fermentable sugars may be considered a potential feedstock for ethanol production. These potential feedstocks include, but are not limited to, starches, plant matter (also called biomass) and food matter.

In some cases the feedstock may be a waste product from another process, such as wood pulp from paper-making or corn-stover from food crops. In other cases feedstocks may be grown specifically as a source of raw material for ethanol production.

Interest in ethanol as a fuel source is not new. In 1896 Henry Ford built his first automobile, the Quadricycle, to run on ethanol. A Model T designed in 1908 contained a carburetor adjustment that could allow it to run on ethanol. The design proved unsuccessful however, as high ethanol taxes led people to favor gas.

Demand for ethanol fluctuates with the rising and falling availability of oil, peaking during times such as World Wars I and II or the energy crisis of the 1970s. In the 1980s, U.S. Congress enacted a series of legislative measures aimed at making ethanol more attractive to potential producers. Today, as concern over the depletion of fossil fuels grows, interest in ethanol as a fuel source is again on the rise. As of January 2005, there were 87 U.S. ethanol plants with a total production capacity of 3,557 million gallons per year. Another 16 plants with a total production capacity of 681 million gallons per year are under construction.

Increasingly, farmers are investigating the value of adding an ethanol production facility to their operations. The benefits to the rural community in terms of job growth and economic opportunity are many. However, most ethanol production today is being done at large centralized processing facilities, because the methods currently used are economically viable only at capacities of 30 million gallons per year or more. There exists a need for more cost-effective ethanol recovery processes that will allow ethanol production to occur at the local level. Such production will bring benefits not only locally, but nationally and globally.

Interest in the production of other light organic compounds, for example acetone and other light alcohols, by fermentation is also increasing. In particular, the use of butanol as a biofuel or fuel additive is of interest.

In some cases, the raw materials that comprise the feedstock used to produce bioethanol may not contain any or sufficient fermentable sugars, so various conversion techniques may be used to obtain fermentable sugars, particularly from cellulosic or lignocellulosic materials. A recent survey of such approaches is given in Mosier et al., "Features of Promising Technologies for Pretreatment of Lignocellulosic Biomass," Bioresource Technology 96, pp 673-686, 2004.

Early work on recovering ethanol from lignocellulose-containing material is described in U.S. Pat. No. 1,323,540, to Brown. The process includes a saccharification step, in which cellulose is broken down to sugars by acid hydrolysis. Numerous other patents describe hydrolysis of cellulosics by acid hydrolysis, enzymatic hydrolysis or other methods. Representative patents include U.S. Pat. Nos. 3,990,945; 4,174,976; 4,409,032; 5,628,830 and 6,333,181.

A recent innovation, known as simultaneous saccharification and fermentation (SSF), combines saccharification and fermentation into one step. U.S. Pat. No. 4,009,075, to Bio-Industries, describes a representative SSF process.

Recovery of ethanol from fermentation broth has been performed traditionally by filtering out solid material, and separating ethanol from water by distillation. U.S. Pat. No. 4,326,036, to Hayes, describes a process for manufacturing ethanol from sugar cane in which a membrane separation step is used to separate ethanol from water by pervaporation, and in which the ethanol-rich permeate vapor from the membrane separation step is passed for purification to distillation/rectification.

U.S. Pat. No. 6,755,975 to the U.S. Environmental Protection Agency and Membrane Technology and Research, Inc., describes a process for separating organic compounds from water using a combination of pervaporation and dephlegmation. The process can be applied to ethanol/water separation. U.S. Pat. No. 6,755,975 is incorporated herein by reference in its entirety.

U.S. Pat. No. 6,899,743, to Membrane Technology and Research, Inc., described a process for separating organic/organic mixtures using a combination of membrane separation and dephlegmation.

SUMMARY OF THE INVENTION

The invention is a process for producing and recovering a light alcohol, especially ethanol, using a combination of steps including fermentation, membrane separation, dephlegmation and dehydration.

In a basic embodiment, the process includes the following steps:

(a) fermenting a sugar to form a fermentation broth comprising the alcohol and water;

(b) performing a first membrane separation step, comprising:
  (i) providing a first membrane having a first feed side and a first permeate side;
  (ii) passing at least a portion of the fermentation broth as a first feed stream across the first feed side under first conditions that provide a first driving force for transmembrane permeation;
  (iii) withdrawing from the first feed side a residue stream depleted in the alcohol compared with the first feed stream;
  (iv) withdrawing from the first permeate side a first permeate stream enriched in the alcohol compared with the first feed stream;

(c) performing a dephlegmation step, comprising:
  (i) providing a dephlegmator adapted for partial condensation of a gas stream by providing countercurrent flow between the rising gas stream and a falling condensate stream;
  (ii) passing at least a portion of the first permeate stream into the dephlegmator as the gas stream;
  (iii) withdrawing from the dephlegmator an overhead stream enriched in the alcohol compared with the gas stream;
  (iv) withdrawing from the dephlegmator a condensate stream depleted in the alcohol compared with the gas stream;

(d) performing a second membrane separation step comprising:
  (i) providing a second membrane having a second feed side and a second permeate side;

(ii) passing at least a portion of the overhead stream across the second feed side under conditions that provide a second driving force for transmembrane permeation;

(iii) withdrawing from the second feed side an alcohol product stream enriched in the alcohol compared with the overhead stream;

(iv) withdrawing from the second permeate side a second permeate stream depleted in the alcohol compared with the overhead stream.

The feedstock to step (a) may be any feed that contains a fermentable sugar.

Preferred sources of feedstock for the sugar of step (a) include waste materials that contain sugar, starch, cellulosic or other substances that can be converted to sugar. These types of waste are diverse, and include: food-processing wastes, such as cheese whey; other agricultural wastes, such as grape skins; and cellulosic wastes, such as corn stover or wood waste. Other examples of feedstocks include biomass that may be grown specifically as a source of raw material for alcohol production, such as cereal grains, grasses, sugarcane and root crops.

Ethanol and other light alcohols can be made and recovered from all of these materials more cost-effectively by the present process than by prior art processes.

The fermentation step may be carried out using any reaction that can convert a sugar to an alcohol. Preferably the reaction is the commonplace enzymatic reaction using yeast to ferment a six-carbon sugar to ethanol. Other representative fermentation reactions include the use of clostridium organisms to produce ABE (acetone-butanol-ethanol). The step may be carried out in any type of batch or continuous mode.

If the source material itself does not contain adequate quantities of sugar, but may be treated to form sugars, the invention may include one or more additional steps to carry out appropriate treatment, such as to convert starch or cellulose to sugar, or to break down lignin and then convert exposed cellulose. These steps may be carried out as pretreatment before the material enters the fermentation vessel, or may be performed simultaneously with the fermentation step.

The feed stream to the first membrane separation operation contains at least a light alcohol and water, and often may contain sugars, salts or other dissolved matter. Preferably, no solid matter should be left in the feed to this step, as it may foul the membranes.

The invention may include one or more filtration steps between the fermentation step and the first membrane separation step, to recover yeast cells, to remove other suspended solid matter that might foul the membranes in the membrane separation step, to remove dissolved nutrients, salts or excess sugar, or otherwise to prepare the feed to the membrane separation step. Depending on the materials to be removed, this filtration step can optionally include one or more of microfiltration, ultrafiltration, nanofiltration or reverse osmosis.

The first membrane separation is carried out using membranes that provide a separation factor in favor of the alcohol over water. In other words, the membranes preferentially permeate the alcohol, such that the permeate stream is alcohol-enriched, and reject water, such that the residue stream is water-enriched. Various membranes that can provide suitable properties, including polymeric membranes and inorganic membranes, are known.

The first membrane separation step can be carried out with the feed as a liquid, a vapor or a two-phase mixture. Transport through the membrane is induced by maintaining the vapor pressure on the permeate side of the membrane lower than the vapor pressure of the feed. Preferably, the separation is carried out in pervaporation mode, in which the feed pressure is such that the feed is liquid, and the permeate pressure is such that the permeate is in the vapor phase.

The vapor pressure difference is usually, but not necessarily, achieved by operating at below atmospheric pressure on the permeate side. A partial vacuum on the permeate side of the membrane may be obtained simply by relying on the pressure drop that occurs as a result of the cooling and condensation that takes place in the dephlegmator, or it may be augmented by use of a vacuum pump. A sweep gas on the permeate side may also be used to lower the concentration of the permeating components. The vapor pressure of the feed liquid may be, and preferably is, raised by heating the feed solution.

The system that carries out this membrane separation step may contain one or more membrane modules, of similar or dissimilar type, and may be arranged in any desired configuration, such as one-stage, multistep or multistage, all of which are known in the membrane separation arts.

The temperature and/or pressure and/or composition of the streams passing from one step or stage to the next may be adjusted. If multiple membrane modules are needed to perform the separation, it is preferred that the modules be housed in a single vessel or assembly, to facilitate heat integration.

The first membrane separation step produces a permeate stream enriched in alcohol compared with the membrane feed stream. Typically, the permeate stream may contain between about 15% and 70% alcohol. This stream forms the feed to the dephlegmation step.

Dephlegmation, also known as reflux condensation, is used to separate alcohol-rich and water-rich fractions from the permeate vapor. In the process of the invention, the dephlegmation step performs two needed functions. By cooling and condensing a portion of the permeate vapor, it both provides a lowered pressure on the permeate side of the membranes of the first membrane separation step and achieves separation of alcohol-enriched vapor from water-enriched condensate.

The ability of the dephlegmation step to lower the permeate pressure is often sufficient to obviate the need for a vacuum pump on the permeate side, thereby simplifying the equipment and reducing the need for relatively high maintenance components to operate the membrane separation step.

A dephlegmator differs from a simple condenser in that only partial condensation occurs, the condensate liquid and the uncondensed vapor leave the dephlegmator separately, and the condensed and uncondensed portions are not in equilibrium with each other. A dephlegmator differs from a distillation column in that most or all of the heat energy required to effect the separation is provided by the incoming vapor itself.

The permeate vapor stream is introduced as a gas-phase feed at or near the bottom of the dephlegmator. The dephlegmator may be of any type capable of providing countercurrent contact between upward flowing vapor and downward flowing condensate, and is preferably able to provide heat exchange over at least part of the length of the dephlegmator between the feed under treatment and an appropriate coolant. Examples of suitable types of dephlegmator include shell-and-tube, plate-fin and packed column.

As the feed vapor rises up the dephlegmator, a portion of the vapor condenses, flows down the walls or packing, and is withdrawn as a water-rich condensate from the bottom of the column. An alcohol-rich vapor, typically containing at least about 80% or 90% alcohol, is withdrawn as an overhead stream from the top of the dephlegmator.

To increase the purity of this raw alcohol product, the overhead is passed to a dehydration step. Preferably, this step is a second membrane separation step, this time using a membrane that is selective in favor of water over alcohol. Again, this separation can be carried out with the feed in the form of a vapor, liquid, or two-phase mixture. Various polymeric and inorganic membranes able to permeate water and reject ethanol are known. Like the first membrane separation step, this step may contain one or multiple membrane modules, and may be configured in any convenient manner. The purified alcohol product, preferably containing at least 97% alcohol and most preferably at least 99% alcohol, is withdrawn as the residue stream from this step.

If further purification of the product is needed, it may be passed to a molecular sieve, for example, for a final polishing treatment. As a less preferred alternative, the entire dehydration step may be performed by molecular sieving.

The various unit steps within the process produce off streams, including the residue stream from the first membrane separation step, the condensate stream from the dephlegmation step and the permeate stream from the second membrane separation or dehydration step. Any of these streams may simply be discharged from the process or may be recirculated within the process as desired and convenient.

In general, it is most preferred to discharge the first residue stream, which is often relatively clean, containing less than 1% alcohol, for example, or to return it to the fermentation step; to recirculate the condensate stream from the dephlegmator to the first membrane separation step; and to recirculate the permeate stream from the dehydration step to the dephlegmation step.

The invention is applicable to alcohol, especially ethanol, production at all scales, but is particularly well suited for small-scale, localized plants with production of less than about 5 or 10 million gallons of alcohol per year. The invention makes possible distributed ethanol production from the thousands of relatively small local sources of biomass and sugar-containing streams that exist throughout rural America and the world.

As it applies to a preferred embodiment for ethanol production, the process of the invention includes the following steps:

(a) fermenting a sugar to form a fermentation broth comprising ethanol and water;
(b) filtering at least a portion of the fermentation broth to produce a filtrate stream;
(c) performing a first membrane separation step, comprising:
(i) providing a first membrane having a first feed side and a first permeate side;
(ii) passing the filtrate stream as a liquid feed stream across the first feed side under first conditions that provide a first driving force for transmembrane permeation;
(iii) withdrawing from the first feed side a residue stream depleted in ethanol compared with the liquid feed stream;
(iv) withdrawing from the first permeate side a first permeate stream enriched in ethanol compared with the liquid feed stream;
(d) performing a dephlegmation step, comprising:
(i) providing a dephlegmator having a coolant flow side and a gas stream flow side and adapted for partial condensation of a gas stream by providing countercurrent flow between the rising gas stream and a falling condensate stream;
(ii) passing at least a portion of the first permeate stream into the dephlegmator as the gas stream;
(iii) flowing a coolant across the coolant flow side in heat-exchanging relationship with the gas stream;
(iv) withdrawing from the dephlegmator an overhead stream enriched in ethanol compared with the gas stream;
(v) withdrawing from the dephlegmator a condensate stream depleted in ethanol compared with the gas stream;
(e) performing a second membrane separation step comprising:
(i) providing a second membrane having a second feed side and a second permeate side;
(ii) passing at least a portion of the overhead stream across the second feed side under conditions that provide a second driving force for transmembrane permeation;
(iii) withdrawing from the second feed side an ethanol product stream enriched in ethanol compared with the overhead stream;
(iv) withdrawing from the second permeate side a second permeate stream depleted in ethanol compared with the overhead stream.

Other objects and advantages of the invention will be apparent from the description of the invention to those of ordinary skill in the art.

It is to be understood that the above summary and the following detailed description are intended to explain and illustrate the invention without restricting its scope.

DETAILED DESCRIPTION OF THE INVENTION

Figure 1:
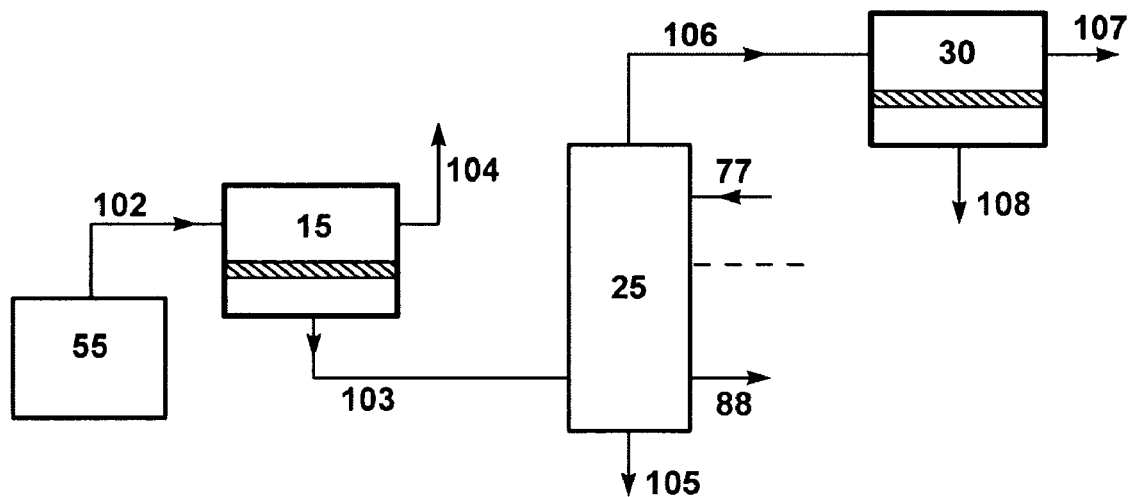
FIG. 1 is a schematic drawing showing a basic embodiment of the invention.

All percentages herein are by weight unless otherwise stated.

The terms dephlegmation and reflux condensation have the same meaning herein.

The terms vapor and gas are used interchangeably herein.

The term cellulosic as used herein refers to material containing cellulose, hemicellulose or lignocellulose.

The term alcohol as used herein refers to a light alcohol containing up to four carbon atoms, or a mixture containing such an alcohol.

The invention is a process for producing and recovering a light alcohol, using a combination of steps including fermentation, membrane separation, dephlegmation and dehydration.

For simplicity of explanation, the invention is described in detail below principally as it relates to the production of ethanol, which the inventors believe is the most useful application of the process. Those of skill in the art will be able to apply the description to the production of other light alcohols, as well as alcohol-containing mixtures, such as ABE, by following the teachings below.

In a basic embodiment as it relates to the production of ethanol, the process of the invention includes the following steps:

(a) fermenting a sugar to form a fermentation broth comprising ethanol;

(b) performing a first membrane separation, comprising separating at least a part of the fermentation broth into an ethanol-rich portion and an ethanol-lean portion;

(c) performing a dephlegmation step, comprising separating the ethanol-rich portion into an overhead stream further enriched in ethanol compared with the ethanol-rich portion and a condensate stream depleted in ethanol compared with the ethanol-rich portion;

(d) performing a second membrane separation, comprising dehydrating the overhead stream into an ethanol product stream and a non-product stream.

The feedstock to step (a) may be any feed that contains a fermentable sugar. By a fermentable sugar, we mean any sugar that can be converted or broken down to simpler sugars and subsequently converted, by the activity of a biological or chemical agent to form an alcohol. Representative common fermentable sugars include, but are not limited to, six-carbon sugars, such as sucrose, fructose, lactose and glucose, and five-carbon sugars, such as xylose and arabinose.

Preferred sources of feedstock for the sugar are the waste materials that are abundant in the agriculture, food, timber, pulp and paper industries. Some of these materials, such as cheese whey and wastes from fruit or vegetable processing, may already contain substantial amounts of sugars. Others may contain no sugars as such, but may contain starch, cellulosic or other substances that can be broken down to simple sugars, as discussed in more detail with respect to FIG. 3 below.

The fermentation step may be carried out using any fermentation agent appropriate to the sugars that are to be fermented. Fermentation agents include microorganisms that give rise to fermentation as part of their metabolic activity, enzymes that act directly to break down and/or convert sugars, and other special chemicals. Where it can be used, the most preferred fermentation agent is yeast.

The fermentation step may be carried out in any convenient manner. Numerous fermentation techniques appropriate for use in alcohol production are well known in the art and described in the literature. For example, design and operation of fermentation reactors, and the parameters and other considerations that must be taken into account in their operation are discussed in H. C. Vogel et al., Fermentation and Biochemical Engineering Handbook, 2nd edition, Noyes, 1996, and in M. Roehr (Ed.), The Biotechnology of Ethanol-Classical and Future Applications, Wiley-VCH, 2000.

If the original feedstock from which the sugar is obtained is starchy or cellulosic, it is preferred to operate the fermentation as part of a simultaneous saccharification and fermentation (SSF) process, as discussed in more detail below with respect to FIG. 3.

In a basic representative form, the fermentation step is carried out by charging the sugar-containing substrate, with additional nutrients if needed, and a yeast culture to the fermentation reactor. The reactor may take the form of a single vessel, or may be staged, for example to provide different fermentation conditions in each stage.

The fermentation reactor may be operated in any mode, such as batch, fed-batch, semi-continuous or continuous mode.

The broth in the fermentation reactor(s) typically comprises an aqueous mixture of ethanol, unreacted sugars, microorganism cells, nutrients, and solid or dissolved contaminant matter that may have been introduced into the reactor in the substrate solution.

The portion of the broth to be passed to the first membrane separation step should preferably contain very little solid matter that can foul the membranes. If the nature and conditions of the fermentation step are such that a relatively clean solution containing nothing but ethanol and water, plus a low concentration of dissolved materials, is present at the end of the fermentation, then it is possible to simply draw off the broth intermittently or continuously and pass it to the membrane separation step. The residue remaining after the first membrane separation can then be returned to the fermentation step or discharged.

If the broth is relatively free of dissolved contaminants and it is only necessary to restrain macroscopic solid matter, the portion of the fermentation broth to be sent to the first membrane separation step may be captured by means of siphoning, decanting or other simple phase-separation technique such that only the liquid components of the fermentation broth are supplied to the membrane separation step.

More commonly, however, the broth will contain at least some fine undissolved solid matter or large solutes. These types of contaminants may be removed by microfiltration, ultrafiltration, nanofiltration, depending on the size and nature of the contaminant, or, if dissolved salts are a problem, by reverse osmosis. The operation of such processes is well known and understood in the art.

As a preferred embodiment, therefore, the invention includes one or more filtration steps of the above-mentioned types between the fermentation step and the membrane separation step, or integrated with the fermentation step.

The steps can be performed in various ways. If a continuous fermentation process is used, for example, a bleed stream may be taken from the fermentation reactor, filtered to produce clear broth for the first membrane separation step, and the residue returned to the fermentor to recover yeast cells and continue the fermentation.

If a batch fermentation process is used, the broth may be filtered, the clean filtrate sent to the first membrane separation step, and the concentrate containing cell debris and other waste matter sent for disposal. A combination of the two techniques may also be used.

The portion of the broth that is passed as feed to the first membrane separation step comprises water and ethanol as major components. The ethanol content may be any value, but typically ranges from a few percent, such as 2%, 4% or 5%, to a relatively high concentration, such as 10%, 15%, 20% or more, depending on the type of fermentation and number of fermentation stages. Generally, the concentration is between about 5% and 20%, and more preferably between about 10% and 15%. Commonly, the concentration is no higher than about 12% or 14%, as higher concentrations of ethanol in the broth suppress fermentation and may kill the yeast.

The first membrane separation step is carried out by passing the broth portion across the feed sides of the membranes under conditions that provide a driving force for transmembrane permeation. This step uses membranes that provide separation factors in favor of ethanol over water. In other words, the membranes preferentially permeate ethanol and reject water. Various membranes that can provide suitable properties are known, including polymeric membranes, inorganic membranes, and mixed membranes, in which inorganic particles are held in a polymeric matrix.

Preferred polymeric membrane materials include rubbery non-crystalline polymers, with glass transition temperatures below the normal operating temperature of the system. Thermoplastic elastomers are also useful. These polymers combine hard and soft segments or domains in the polymer structure. Provided the soft segments are rubbery at the temperature and operating conditions of the invention, polymers of this type could make suitable membranes for use in the invention.

Polymers that may be used include, but are not limited to, nitrile rubber, neoprene, polydimethylsiloxane (silicone rubber), chlorosulfonated polyethylene, polysilicone-carbonate copolymers, fluoroelastomers, plasticized polyvinylchloride, polyurethane, cis-polybutadiene, cis-polyisoprene, polychloroprene, poly(butene-1), ethylene-propylene copolymers and terpolymers, polystyrene-butadiene copolymers, styrene/butadiene/styrene block copolymers, styrene/ethylene/butylene block copolymers, thermoplastic polyolefin elastomers, polyesteramides, and block copolymers of polyethers and polyesters.

The most preferred rubbery polymer membrane material is silicone rubber.

Another type of membrane that has been reported to provide good pervaporation separation factors for ethanol over water, indeed much higher than silicone rubber, is a rubbery membrane impregnated with small hydrophobic zeolite particles, such as silicalite particles. Such membranes, sometimes referred to as mixed matrix membranes, are described in U.S. Pat. No. 4,925,562, assigned to GFT Gesellschaft fur Trenntechnik mbH, and are now offered commercially by Sulzer Chemtech, of Winterthur, Switzerland.

Yet another type of preferentially organic permeating membrane that can be used is an entirely inorganic membrane, such as a tubular membrane comprising a hydrophobic zeolite layer or particles. Such membranes are described, for example, in J. Caro et al., "Zeolite membranes—state of their development and perspective", *Microporous and Mesoporous Materials*, Vol. 38, 3-24, 2000.

The membrane may take the form of a homogeneous membrane, an asymmetric membrane, a multilayer composite membrane, a matrix incorporating a gel or liquid layer, or any other form known in the art. If the membranes are polymeric membranes, a particularly preferred form is a composite membrane, comprising at least a microporous, relatively unselective support layer and a thin selective coating layer, and optionally other layers, such as a backing, a gutter layer, and a sealing or protective top layer. The making of such membranes is well known in the art.

The membranes may be formed as flat sheets, hollow fibers, tubular membranes or any other convenient form, and housed in any appropriate cartridge or module configuration, such as a spiral-wound module, a plate-and-frame module or a potted hollow-fiber cartridge. In a preferred embodiment for polymeric membranes, the membranes are cast and coated as flat sheets, and then rolled into spiral-wound modules. The preparation of spiral-wound modules is well known in the art. A preferred form for inorganic membranes is a ceramic tubular module, as is well known in the art.

The membrane separation unit used for the first membrane separation step can include a single membrane module or a bank or array of multiple membrane modules. A single bank of membrane modules is usually adequate to meet the processing requirements for many applications. If additional processing is desirable, an array of modules with multiple sub-steps or -stages, with recycle of intermediate streams, as is known in the art, may be used. For example, if the residue stream requires further purification, it may be passed to a second bank of membrane modules for a second processing sub-step. Such an arrangement is preferred if the feed stream requires reheating as it passes along the train of modules, or if it is desired to recirculate a stream from the dephlegmation or dehydration steps and match stream compositions, for example.

The first membrane separation step can be carried out with the feed as a liquid, a vapor or a two-phase mixture. Preferably, the separation is carried out in pervaporation mode, in which the feed pressure is such that the feed is liquid, and the permeate pressure is such that the permeate is in the vapor phase.

Transport of a component through the membrane takes place under conditions that provide a driving force for transmembrane permeation, the pressure of the component on the permeate side of the membrane being lower than the pressure on the feed side. The pressure difference is usually, but not necessarily, achieved by operating at below atmospheric pressure on the permeate side. A partial vacuum on the permeate side of the membrane may be obtained simply by relying on the pressure drop that occurs as a result of the cooling and condensation that takes place in the dephlegmator, or it may be augmented by use of a vacuum pump. A sweep gas on the permeate side may also be used to lower the concentration of the permeating components. The vapor pressure of the feed liquid may be, and preferably is, raised by heating the feed solution.

The temperature and/or pressure and/or composition of the streams passing from one step or stage to the next may be adjusted. If the membrane is operated under pervaporation conditions, the feed liquid may need to be reheated between membrane modules or banks of modules, to maintain the partial pressure driving force for permeation. Heat integration may be facilitated by housing the membrane modules together in a single assembly.

If the membrane separation step is operated in gas separation mode, the broth that has been drawn off from the fermentation step is heated to convert it to a superheated vapor before it is introduced into the membrane separation step. If the feed vapor temperature is very high, such as above about 130° C. or 150° C., a polymeric membrane may be unable to withstand the high temperature and inorganic membranes are preferred or required.

Vapor phase membrane separation, like pervaporation, is a pressure-driven process, that is, transport through the membrane is induced by maintaining the vapor pressure on the permeate side of the membrane lower than the vapor pressure of the feed liquid. If the feed is at 125° C., for example, the vapor pressure will be in the range about 2-5 atm, depending on the composition. If the feed vapor is at 150° C., the vapor pressure will be in the range about 5-10 atm, and if the feed temperature is 220° C., the vapor pressure will be in the range about 25-60 atm.

In many cases, maintaining the permeate side of the membrane at atmospheric pressure, will, therefore, provide adequate transmembrane driving force. If a greater vapor pressure difference is required, this may be obtained by operating under partial vacuum in similar manner to that described above with respect to pervaporation applications, or by sweeping the permeate side of the membrane with gas or steam.

Whether operated in pervaporation or gas separation mode, the first membrane separation step produces a permeate stream enriched in ethanol compared with the membrane feed stream that forms the feed to the dephlegmator. Typically, this stream contains between about 30% and 60% ethanol. This step also produces a residue stream depleted in ethanol and enriched in water. This residue stream typically contains a very low concentration of ethanol, such as less than 1% ethanol, and is preferably recycled to the fermentation tank to dilute the broth or discharged from the process. It may simply be sent to the municipal sewer, for example, or may be returned elsewhere in the facility where dilution is useful or acceptable.

The ethanol-enriched permeate is passed as feed to dephlegmation step (c).

Dephlegmation, also known as reflux condensation, differs from simple full condensation in that only partial condensation occurs, the condensate liquid and the uncondensed vapor leave the dephlegmation step separately, and the condensed and uncondensed portions are not in equilibrium with each other. The process relies on a, usually, downward flowing condensate reflux stream to provide cooling and condensation of a, usually, upward flowing vapor stream, thereby improving the overall separation between components.

Dephlegmation can take place in any tower or column able to provide direct heat and mass transfer contact between the condensate and vapor streams, and this equipment is referred to as a dephlegmator. Energy is provided to the operation by introducing the feed to be treated into the dephlegmator in vapor form, thereby carrying in the latent heat associated with the vapor. The reflux may be enhanced by adding indirect heat-exchange against a circulating coolant internal or external to the column.

In the present invention, the dephlegmation step serves two functions. One is to separate the permeate vapor into an alcohol-rich vapor and a water-rich condensate. The other is to provide or supplement the driving force for transmembrane permeation in the first membrane separation step. This effect is achieved because the dephlegmator is in fluid communication with the permeate side of the membranes, so the cooling and condensation of permeate vapor that takes place in the dephlegmation step lowers the pressure on the permeate side, thereby increasing the pressure difference across the membrane.

This combined function could not be achieved if a distillation column, operating on a liquid feed, were used instead of the dephlegmator.

To apply the principles of dephlegmation to the present invention, the permeate stream from the first membrane separation step is introduced as the vapor feed at or near the bottom of the dephlegmator. In the preferred mode of operation, the dephlegmator is operated in the traditional manner, using heat energy provided solely by the incoming permeate vapor.

Depending on the specific properties of the vapor to be treated, however, a small heater or reboiler may be provided to revaporize part of the condensate and return the vapor to the column, thereby augmenting the heat energy supply to the column. In this case, the additional energy supplied in this manner should represent no more than 20%, more preferably no more than 15%, and yet more preferably no more than 10% of the total heat energy supplied to the column by the permeate vapor stream and the return vapor stream.

In other words, at least 80%, more preferably 90%, and most preferably all, of the heat supplied to the dephlegmator should come from the permeate vapor stream.

Preferably, but not necessarily, the dephlegmator is adapted to provide cooling by heat exchange, as mentioned above, between the feed under treatment and an appropriate coolant, over at least part of the column length. As another option, a small heat exchanger external to the column may be provided and used to condense a portion of the overhead vapor leaving the column. The condensate may then be reintroduced as reflux to the column. Any cooling agent may be used as heat-exchange agent, although simple cooling water is preferred.

When the dephlegmator is in use, the vapor feed is introduced, usually at or near the bottom of the dephlegmator. The coolant stream, if used, is introduced at or near the top of the dephlegmator and flows down a coolant channel or channels that are in heat-exchanging relationship with the channels carrying the upward-flowing feed stream.

Warm membrane permeate vapor passes into the column and rises in the feed passages or channels. A portion of the vapor condenses on the comparatively cold tube or channel walls or packing surfaces; this condensate runs downward within the feed passages, countercurrent to the feed vapor. Mass transfer between the condensate liquid and the vapor enriches the down-flowing liquid in water and the up-flowing vapor in ethanol.

The liquid condensate, enriched in water, exits the dephlegmation step as a bottom stream from the column. This stream may be discharged from the process, but is more preferably recirculated within the process, as described in more detail with respect to FIG. 4 below.

The vapor stream, enriched in ethanol, exits the dephlegmation step as a raw overhead product stream. Typically, but not necessarily, this vapor will contain at least about 80 wt % ethanol, and more preferably at least 90 wt % ethanol.

Examples of suitable types of dephlegmator include shell-and-tube, plate-fin and packed column. The shell-and-tube design, with or without structured packing in the feed channels, is preferred.

Further details of dephlegmator types and operating conditions and preferences for the dephlegmation step may be found in U.S. Pat. No. 6,755,975, incorporated herein by reference in its entirety, and U.S. Pat. No. 6,899,743, particularly FIGS. 8 and 9 and the text that describes them, these figures and text being incorporated herein by reference.

Theoretical treatments on the basis of which suitable operating conditions may be calculated by the skilled person are found, for example, in (i) S. Di Cave et al., "Mathematical Model for Process Design and Simulation of Dephlegmators (Partial Condensers) for Binary Mixtures", Canadian Journal of Chemical Engineering, Vol. 65, 559-564, 1987; (ii) R. J. Jibb et al., "The Potential for Using Heat Transfer Enhancement in Vent and Reflux Condensers", (available from web site of Cal Galvin Ltd. at http://www.calgavin.co.uk/news): and (iii) G. A. Lucadamo et al., "Improved ethylene and LPG recovery through dephlegmator technology", Gas Separation and Purification, Vol. 1, 94-102, 1987.

To increase the purity of the raw ethanol product stream, the overhead from the dephlegmation step is passed to a dehydration step. Preferably, this step is a second membrane separation step, this time using a membrane that is selective in favor of water over ethanol.

A number of suitable water-selective materials are known for use in dehydration membranes. Polyvinyl alcohol (PVA) is the most commonly used commercial material. Another polymer that has sometimes been used is cellulose acetate. Yet other suitable membrane include chitosan membranes, ion-exchange membranes, such as Nafion® membranes, and membranes incorporating fluorinated selective layers.

Inorganic membranes comprising hydrophilic materials may also be used as dehydration membranes. Such membranes include amorphous silica membranes and membranes including a water permeating zeolite layer, such as ZSM-5. Such membranes are also discussed in the Caro et al. paper above, and have been developed commercially, for example, by the Mitsui and Company of Japan.

Various types of inorganic membranes may be purchased from Mitsui and Company (USA) of New York, Isotronics of Paradise Valley, Ariz., Sulzer Chemtech Membrane Systems, based in Heinitz, Germany, and Pervatech BV of Enter, Netherlands.

The membrane separation unit can include a single membrane module or a bank or array of modules with multiple sub-steps or -stages.

Splitting the dehydration step into two sub-steps, with the residue from the first sub-step being passed as feed to the second sub-step, is often preferred in that it enables a very high ethanol concentration (>99% ethanol) to be achieved in the product stream, and at the same time provides two separate permeate streams with significantly different compositions that may be recycled to different destinations within the process.

For example, the permeate from the first sub-step may contain about equal amounts of ethanol and water and may be recirculated to the dephlegmation step; the permeate from the second sub-step may be relatively rich in ethanol and can be returned to the inlet of the first sub-step to increase product recovery.

Like the first membrane separation step, the dehydration step can be carried out with the feed that is passed across the membranes being in the form of a liquid, a vapor or a two-phase mixture. If the overhead from the dephlegmator is cooled, compressed or both to liquefy the feed stream to the membranes, the step is carried in pervaporation mode. In this case, the feed liquid will typically need to be reheated after condensation to raise the vapor pressure, and hence driving force for transmembrane permeation, before it is passed into the membrane unit.

If the step is carried out with the overhead still in the vapor phase, the stream will usually need to be compressed, as the vapor emerging from the dephlegmator overhead is typically at relatively low pressure. A compressor will then be needed to compress the stream, but the hot high-pressure condition of the stream will provide good transmembrane driving force, and high transmembrane fluxes. Depending on site or separation specifics, either mode of operation may be preferred.

The purified ethanol product is withdrawn as the final residue stream from this step. The ethanol content of this stream is usually, and preferably, at least 97% ethanol, and more preferably higher, such as 99% or 99.5% ethanol.

The second membrane separation step also produces one or more permeate streams, which will contain water and ethanol, but may also contain small amounts of fusel oil, other alcohols, light esters and the like that were produced as ancillary fermentation products during the fermentation step. The permeate may be discharged from the process, but is more preferably recirculated within the process, as described in more detail with respect to FIG. 4 below.

If further purification of the product is still needed, it may be passed to a molecular sieve or the like for a final polishing treatment. As a less preferred alternative, the entire dehydration step may be performed by molecular sieving.

The process of the invention in various embodiments is shown in FIGS. 1-4. It will be appreciated by those of skill in the art that these are very simple schematic diagrams, intended to make clear the key aspects of the invention, and that an actual process train will usually include many additional components of a standard type, such as heaters, chillers, condensers, pumps, blowers, other types of separation and/or fractionation equipment, valves, switches, controllers, pressure-, temperature-, level- and flow-measuring devices and the like.

A basic embodiment is shown in FIG. 1. Referring now to FIG. 1, a feed stream 102 containing ethanol and water, is transferred from a fermentation step or unit 55, to a pervaporation step or unit 15. This step separates stream 102 into a permeate stream, 103, which is relatively rich in ethanol and depleted in water compared to stream 102, and a residue or retentate stream, 104, which is depleted in ethanol and enriched in water relative to stream 102.

Stream 104 can pass to any destination. For example, it may be discharged as waste, returned to the fermentor, directed to another process, or recycled in part or in whole in a loop around the pervaporation step.

The ethanol-enriched stream 103 is sent to a dephlegmation step or unit, 25. Stream 103 is introduced as a feed stream into the dephlegmator at or near the bottom of the unit. The representative dephlegmation step of FIG. 1 is assumed to be carried out using equipment of the type shown in FIG. 8 of U.S. Pat. No. 6,899,743, that is, essentially a simple vertical heat exchanger with external cooling provided over the length of the dephlegmator.

A coolant stream, 77, is introduced at or near the top of the dephlegmator and flows down a coolant channel or channels that are in a heat-exchanging relationship with the channels carrying the upward feed stream 103. The coolant exits the dephlegmator at the bottom as stream, 88. As one possible alternative, it is possible to provide external cooling only in the upper portion of the dephlegmator, and to rely on the cool falling condensate to simultaneously provide both heat and mass transfer with the warm rising vapor in the lower portions of the dephlegmator. In this case stream 88 will be withdrawn higher up the dephlegmator column, as indicated by the dashed line in FIG. 1.

Liquid condensate, enriched in water, exits the dephlegmation step as bottom stream, 105. This stream may be discharged from the process, directed to another process, or more preferably, recirculated within the process, such as to the first membrane separation step.

Vapor stream 106, enriched in ethanol, exits the dephlegmation step as an overhead product stream and is passed to a second membrane separation step, 30, for dehydration. This step separates stream 106 into a retentate stream, 107, which forms the purified ethanol product, and a permeate stream, 108, enriched in water relative to stream 106, which may be discharged or recirculated within the process.

Figure 2:
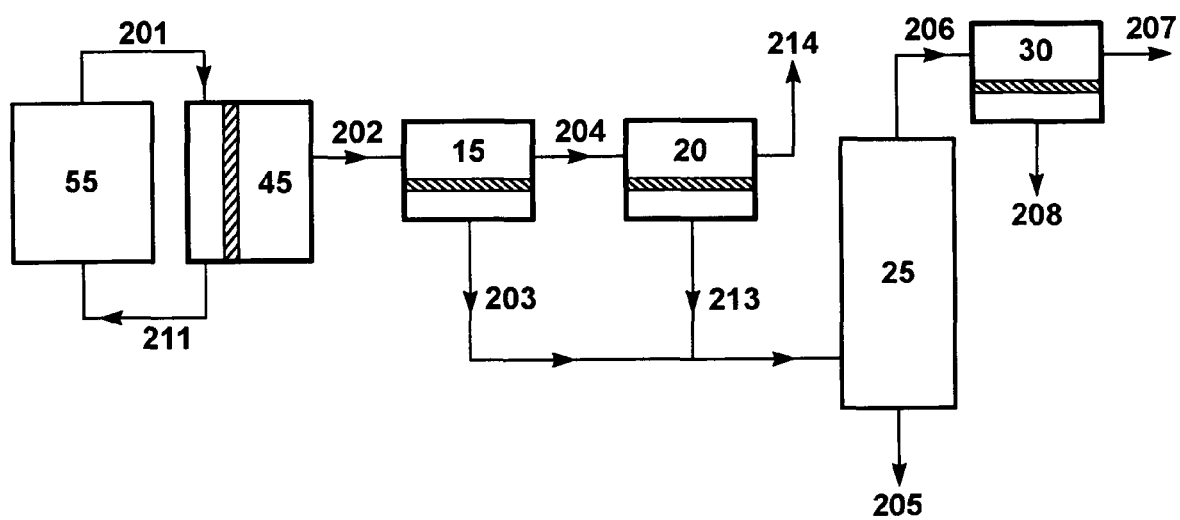
FIG. 2 is a schematic drawing showing a preferred embodiment of the invention in which a filtration step is used to remove material from the filtration broth before it is sent to the first membrane separation step.

A preferred embodiment of the invention, in which a filtration step is used to remove unwanted material from the feed to the first membrane separation step is shown in FIG. 2. The filtration step may be microfiltration, ultrafiltration, nanofiltration, reverse osmosis or any combination of appropriate filtration operations.

Stream, 201, from the fermentation step, 55, is sent to the filtration step(s) or unit, 45, where solids are removed, creating a solids-reduced filtrate stream, 202, and a solids-containing retentate stream, 211. FIG. 2 shows a preferred continuous mode of operation, in which the filtration step also serves as a selective bleed to reduce fermentation inhibition caused by the ethanol. After ethanol removal in stream 202, retentate stream, 211, is returned to the fermentation vessel(s). If this mode of operation is not desired for any reason, stream 211 could simply be discharged.

The filtrate stream is sent to the first membrane separation step. In the preferred embodiment represented in FIG. 2, this pervaporation step is performed in two sub-steps, using membranes that provide a separation factor in favor of ethanol over water. From filtration step 45, stream 202 is sent to first membrane separation sub-step, 15. The permeate, 203, now enriched in ethanol relative to stream 202, is sent to the dephlegmation step, 25. Residue stream, 204, now enriched in water relative to stream 202, is sent to the second membrane sub-step, 20, to undergo further ethanol removal. This sub-step produces a permeate stream, 213, that is pooled with permeate 203 and sent to the dephlegmation step. Residue stream, 214, from this sub-step may be discharged or recycled.

To maintain a high concentration of ethanol in the dephlegmator feed, stream 213 may optionally be recirculated to the feed inlet of membrane bank 15 and mixed with stream 202, instead of pooling with stream 203. One benefit of carrying out the membrane separation in two sub-steps as shown is that stream 204 may be reheated before passing to membrane bank 20. Reheating helps to maintain transmembrane driving force and hence ethanol flux.

Dephlegmation step, 25, may be carried out in any manner described above, and may optionally, but not necessarily, include coolant flow as shown in FIG. 1. This step produces bottoms stream, 205, which may be discharged or recirculated, and ethanol-rich overhead stream, 206, which is passed for dehydration to the second membrane separation step, 30. This step produces an ethanol product stream, 207, and a water-enriched permeate stream, 208, which may be recirculated or discharged.

Figure 3:
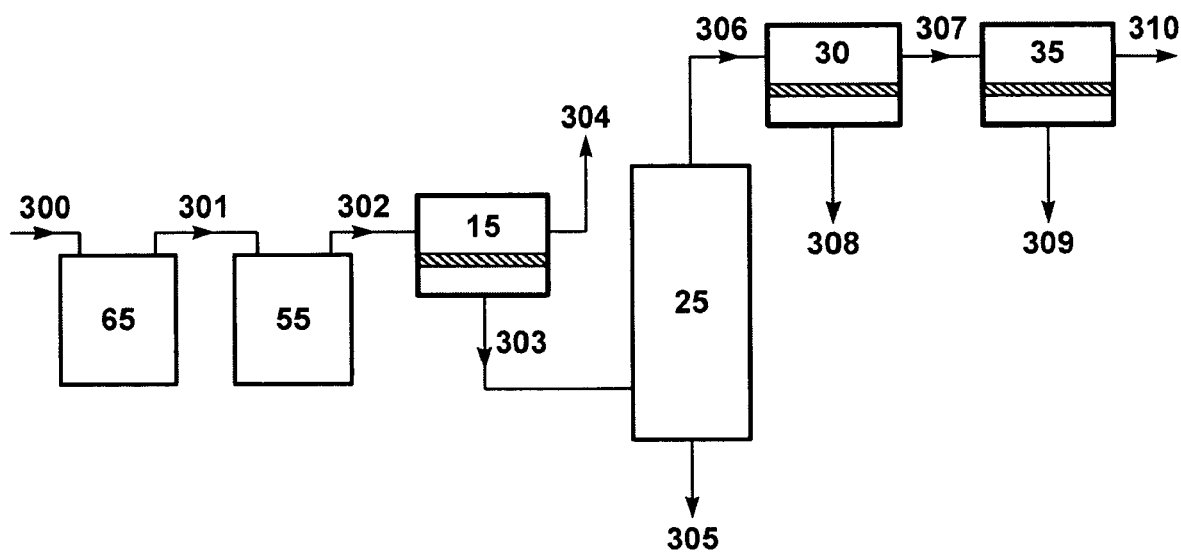
FIG. 3 is a schematic drawing showing an embodiment of the invention including a hydrolysis step to break down waste biomass into fermentable sugars.

An embodiment of the invention in which the feedstock for the fermentation step is waste biomass or other carbohydrate-containing material, and in which the carbohydrate must first be converted to sugar, is shown in FIG. 3. Referring to this figure, the raw starchy, cellulosic or other appropriate feedstock, 300, is introduced into a conversion step, 65.

This step may include any step, or more commonly series of steps, capable of breaking down at least part of the carbohydrate content of the raw feedstock, such steps including, but not limited to, acid hydrolysis, enzymatic hydrolysis and thermochemical conversion. These processes are known to those skilled in the art, and are described in brief below.

If the material to be converted is starchy, simple hydrolysis by heating in water may be adequate to break down the cell walls. Enzymes may then be added to convert the freed starch to sugar. Acid hydrolysis may also be used to convert starchy materials.

If the material to be converted is cellulosic, pretreatment with acids, alkalis or organic solvents is usually required to break apart and separate the hemicellulose, cellulose and lignin in the biomass. Thereafter, hydrolysis of various types can be used to convert the cellulose components.

Dilute acid hydrolysis is a simple, traditional method that provides good conversion efficiency for both starchy and cellulosic materials. It is usually conducted in two stages, to avoid degradation of the sugars produced from hemicellulose under the harsher conditions needed to convert cellulose. In the first stage, dilute sulfuric acid (usually 1% acid or less) is added to the raw feedstock and the mixture is heated, typically to about 200° C. In this stage, hemicellulose is broken down. In the second stage, higher temperatures are used to break down more resistant cellulose materials. Further details of dilute acid hydrolysis can be found in U.S. Pat. No. 4,174,976, for example.

Concentrated acid hydrolysis uses acid concentrations of around 70% in the first stage, but operates at much lower temperatures of around 35-50° C. In the second stage, a lower acid concentration of about 30-40% is used. Concentrated acid hydrolysis can achieve higher conversion rates than dilute acid hydrolysis, but is more complicated to operate. Further details of concentrated acid hydrolysis can be found in U.S. Pat. No. 4,199,371, for example.

Enzymatic hydrolysis uses cellulase enzymes to break down cellulose. Enzymatic hydrolysis is effective under mild operating conditions, but requires days rather than hours to achieve useful conversion levels. The hydrolysis can be done as a discrete step, as represented in FIG. 3, and the converted feed introduced to the fermentation reactor. Alternatively and preferably, the conversion to sugar (saccharification) and the fermentation may be carried out simultaneously in the same vessel(s) by the relatively new process know as simultaneous saccharification and fermentation (SSF). SSF is described in more detail in U.S. Pat. No. 5,100,791, for example.

Thermochemical conversion usually involves gasification of the feedstock to form a synthesis gas containing carbon dioxide, hydrogen and carbon monoxide that is then converted catalytically or by specialized fermentation into ethanol. Most of these processes are still at the development stage and are less preferred.

Referring again to FIG. 3, a converted biomass stream 301 is sent to fermentation step, 55, where it undergoes fermentation. Fermented broth, 302, is sent to the first membrane separation step or unit, 15. (Alternatively, the feed may first be sent through a filtration step as in the embodiment of FIG. 2). Residue stream, 304, from this step may be discharged or recirculated.

The permeate stream, 303, relatively rich in ethanol and depleted in water compared to stream 302, is passed as feed vapor to dephlegmation step or unit, 25. Liquid condensate, enriched in water, exits the dephlegmation step as bottom stream, 305, and may be discharged or recirculated.

Vapor stream, 306, is withdrawn from the dephlegmation step as a raw overhead product stream and passed to the second membrane separation step. In the preferred embodiment in FIG. 3, the second membrane separation step is carried out in two sub-steps, 30 and 35. Stream 306 is sent to first membrane dehydration sub-step, 30. Water enriched permeate, 308, from this sub-step is discharged or recycled within the process. Ethanol enriched retentate stream, 307, is further separated by passing it to the second membrane sub-step, 35. Ethanol enriched retentate stream, 310, from this sub-step is the final ethanol product. The water enriched permeate, 309, is discharged or recycled within the process.

Figure 4:
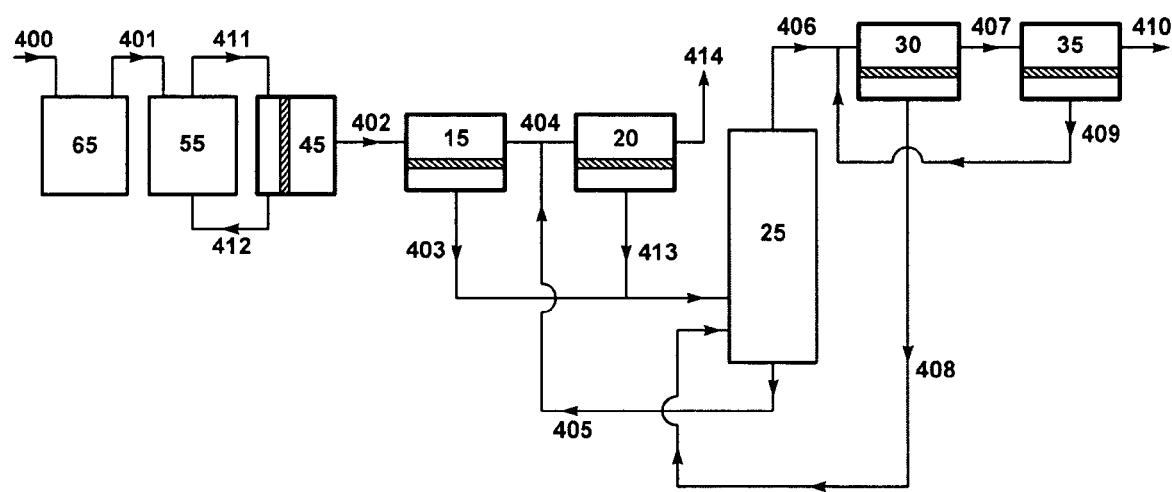
FIG. 4 is a schematic drawing showing a preferred embodiment of the invention in which both the condensate stream and the dehydration step permeate stream are recycled within the process.

A particularly preferred embodiment, in which the process produces only a high-purity ethanol product stream and a dischargeable water stream, with all other streams being recirculated within the process, is shown in FIG. 4. This embodiment assumes that the raw feedstock requires conversion of carbohydrates to sugars, as in the embodiment of FIG. 3, plus a filtration step as in FIG. 2, and that both membrane separation steps are performed in two sub-steps. It will be clear to those of skill in the art that this is merely representative, and that recirculaton of one or more process streams could be carried out in any embodiment of the process, including the basic embodiment of FIG. 1.

Referring to FIG. 4, feedstock stream, 400, enters the process and is sent to conversion step, 65. Sugar-containing stream, 401, from this step passes as feed to fermentor or fermentation step, 55, to undergo fermentation. Fermented broth, 411, is sent to filtration step, 45, resulting in filtrate stream, 402, and a relatively solids-laden retentate stream, 412. Stream 412 is returned to the fermentor, and filtrate 402 is sent to the first sub-step, 15, of the first membrane separation step.

The permeate, 403, from this step, now enriched in ethanol relative to stream 402, is sent to dephlegmation step, 25. Residue stream, 404, enriched in water and depleted in ethanol relative to stream 402, is sent to a second membrane sub-step, 20, preferably after reheating. The permeate stream, 413, from this sub-step is pooled with stream 403 and sent to the dephlegmation step. The residue stream, 414, is discharged.

Streams 403 and 413 are introduced into dephlegmator, 25, at or near the bottom of the unit. Liquid condensate, enriched in water, exits the dephlegmator as bottoms stream, 405. This stream, which has an ethanol concentration similar to that of stream 404, is recirculated between the membrane sub-steps as shown.

The overhead stream, 406, from the dephlegmation step passes to the first sub-step, 30, of the membrane dehydration step. Water-enriched permeate stream, 408, exits this sub-step and is recirculated as vapor to the dephlegmation step. Ethanol-enriched retentate, 407, is passed to the second dehydration sub-step, 35, for further water removal. Dehydrated ethanol stream, 410, is withdrawn as the purified ethanol product of the process. Permeate stream, 409, from the second sub-step is returned to the front of first dehydration sub-step 30.

The invention is now further described by the following examples, which are intended to be illustrative of the invention, but are not intended to limit the scope or underlying principles in any way.

EXAMPLES

Example 1

Ethanol Removal with Composite Membranes

Composite membranes were prepared using standard casting and coating techniques. Polyvinylidene fluoride (PVDF) was used as the support in each case.

One membrane was prepared using polydimethylsiloxane (PDMS) as the selective layer. Other membranes were prepared using silicalite-1 zeolites available from Zeolyst International (P.O. Box 830, Valley Forge, Pa., 19482) in a PDMS polymer matrix as the selective layer. All membranes were prepared by solution-coating the selective layer onto the support layer to generate the following samples:

Sample 1: PDMS on PVDF

Sample 2: A single coat of 20 wt % solution containing polydimethylsiloxane (PDMS) and zeolite in a ratio of 1:1 was applied to PVDF. The thickness of the selective layer was about 80 μm.

Sample 3: A double coat of 20 wt % solution containing PDMS and zeolite in a ratio of 2:1 was applied to PVDF. The thickness of the selective layer was about 150 μm.

The membranes were cut into 12.6 cm² stamps and tested in a permeation test-cell apparatus. An ethanol/water feed stream containing 8.3 wt % ethanol was introduced to the sample membranes in the test cell at a temperature of 75° C. The permeate pressure was maintained at 3.5 torr using a vacuum pump. The fluxes of the membranes were measured, and the selectivities and separation factors were calculated. Results for the samples are shown in Table 1.

TABLE 1

| Sample | Membrane flux (kg/m²h) | Ethanol permeate concentration (wt %) | Ethanol permeance (gpu) | Ethanol/water separation factor | Ethanol/water selectivity |
| --- | --- | --- | --- | --- | --- |
| 1 | 4.35 | 37.8 | 1,900 | 7 | 0.64 |
| 2 | 0.89 | 63.0 | 709 | 19 | 1.77 |
| 3 | 0.90 | 70.0 | 801 | 26 | 2.44 |

As can be seen, the double coated membrane exhibits a selectivity and an ethanol/water ration factor almost 4 times higher than the PDMS membrane without zeolites.

Example 2

Ethanol Dehydration with Perfluorinated Composite Membranes

Commercial membranes were purchased and composite membranes were prepared using standard casting and coating techniques to yield the following samples:

Sample 4: Celfa CMC VP-31 (A commercial polymer membrane from CM Celfa, Switzerland)

Sample 5: 0.5 wt % Cytop® (Asahi Glass Co. Ltd. 1-12-1, Yurakucho, Chiyoda-ku, Tokyo 100-8405 Japan) and 1 wt % Teflon® AF 2400 (Dupont, 1007 Market St. Wilmington, Del., 19898) on PVDF.

Sample 6: 0.5 wt % Hyflon® (Solvay Solexis, Inc., 10 Leonard Lane, Thorofare, N.J. 08086) and 1 wt % Teflon AF 2400 on PVDF.

Sample 7: 1 wt % Teflon® AF 1600 on PVDF

Sample 8: 1 wt % Teflon® AF 1300 on PVDF

The membranes were cut into 12.6 cm² stamps and tested in a permeation test-cell apparatus. An ethanol/water feed stream containing 7.0 wt % ethanol was introduced to the sample membranes in the test cell at a temperature of 75° C. The permeate pressure was maintained at 3.5 torr using a vacuum pump. The fluxes of the membranes were measured, and the selectivities were calculated. Results for the samples are shown in Table 2.

TABLE 2

Ethanol Dehydration by Perfluorinated Membranes

| Sample | Membrane flux (kg/m²h) | Water permeate concentration (wt %) | Water permeance (gpu) | Water/ethanol separation factor | Water/ethanol selectivity |
|---|---|---|---|---|---|
| 4 | 0.63 | 93.2 | 3,270 | 182 | 238 |
| 5 | 0.15 | 88.0 | 400 | 97 | 106 |
| 6 | 0.26 | 85.7 | 1,170 | 80 | 65 |
| 7 | 1.29 | 65.3 | 2,700 | 25 | 27 |
| 8 | 0.60 | 69.6 | 1,470 | 35 | 31 |

Example 3

Modeling Calculations for Dephlegmator

A computer calculation was performed with a modeling program, ChemCad V (ChemStations, Inc., Houston, Tex.), to compare the performance of a dephlegmator with and without supplementary heat supply for the separation of a 1,000 kg/h permeate vapor stream containing 30% ethanol, 70% water. The stream was assumed to be at a temperature of 80° C. and a pressure of 0.1 atm, which pressure was assumed to be maintained throughout the dephlegmator.

The dephlegmator was assumed in both calculations to use heat exchange against a coolant at the top of the column to provide a condensate reflux. In the first calculation, heat energy was assumed to be supplied only by the permeate vapor stream, which has a latent heat of 1.035 kmol.

In the second calculation, heat energy was also assumed to be supplied by the permeate vapor stream. In this calculation, however, the heat energy was supplemented by a vapor stream from a small reboiler at the base of the column that vaporizes a portion of the condensate. The supplementary heat supplied in this way was assumed to be about 10% of the heat supplied by the permeate vapor stream.

The results of the calculations are shown below. Stream numbers refer to FIG. 1.

TABLE 3

Dephlegmator performance comparison

| Stream | 103 | 105 Condensate | | 106 Overhead product | |
|---|---|---|---|---|---|
| | Permeate vapor | No reboiler | With reboiler | No reboiler | With reboiler |
| Temp (° C.) | 80 | 43 | 46 | 30 | 30 |
| Flow rate (kg/h) | 10,000 | 6,680 | 6,477 | 3,321 | 3,523 |
| Component (wt %): | | | | | |
| Ethanol | 30 | 2.6 | 0.08 | 85 | 85 |
| Water | 70 | 97.4 | 99.9 | 15 | 15 |
| Component flow rate (kg/h)h: | | | | | |
| Ethanol | 3,000 | 176 | 5.0 | 2,823 | 2,995 |
| Water | 7,000 | 6,501 | 6,471 | 498 | 529 |

Heat energy supplied by permeate vapor stream=$(1.035 \times 10^4 \times 454)10^3$ Mcal/h=4,700 Mcal/h Heat energy supplied by reboiler vapor stream=475 Mcal/h As can be seen, adding a relatively small amount of supplementary heat cuts the ethanol loss in the condensate from 176 kg/h to 5 kg/h.

We claim:

1. A process for producing a light alcohol, comprising the following steps:
    (a) fermenting a sugar to form a fermentation broth comprising the alcohol and water;
    (b) performing a first membrane separation step, comprising:
        (i) providing a first membrane having a first feed side and a first permeate side;
        (ii) passing at least a portion of the fermentation broth as a first feed stream across the first feed side under first conditions that provide a first driving force for transmembrane permeation;
        (iii) withdrawing from the first feed side a residue stream depleted in the alcohol compared with the first feed stream;
        (iv) withdrawing from the first permeate side a first permeate stream enriched in the alcohol compared with the first feed stream;
    (c) performing a dephlegmation step, comprising:
        (i) providing a dephlegmator adapted for partial condensation of a gas stream by providing countercurrent flow between the rising gas stream and a falling condensate stream;
        (ii) passing at least a portion of the first permeate stream into the dephlegmator as the gas stream;
        (iii) withdrawing from the dephlegmator an overhead stream enriched in the alcohol compared with the gas stream;
        (iv) withdrawing from the dephlegmator a condensate stream depleted in the alcohol compared with the gas stream;
    (d) performing a second membrane separation step comprising:
        (i) providing a second membrane having a second feed side and a second permeate side;
        (ii) passing at least a portion of the overhead stream across the second feed side under conditions that provide a second driving force for transmembrane permeation;
        (iii) withdrawing from the second feed side an alcohol product stream enriched in the alcohol compared with the overhead stream;
        (iv) withdrawing from the second permeate side a second permeate stream depleted in the alcohol compared with the overhead stream.

2. The process of claim 1, wherein the sugar has been prepared by conversion of a plant biomass that comprises a starch or a cellulose.

3. The process of claim 2 wherein the biomass is derived from a plant selected from the group consisting of corn, rice, grapes and trees.

4. The process of claim 1, wherein the sugar is from a cheese whey.

5. The process of claim 1, wherein step (a) is carried out as part of a simultaneous saccharification and fermentation process.

6. The process of claim 1 wherein step (a) is carried out using a microorganism.

7. The process of claim 1, wherein step (a) is carried out using an enzymatic fermentation agent.

8. The process of claim 1, wherein step (a) is carried out using a yeast.

9. The process of claim 1, wherein the alcohol is ethanol.

10. The process of claim 1, wherein the alcohol comprises a mixture of ethanol, iso-propanol and a butanol.

11. The process of claim 1, wherein the alcohol comprises a mixture of ethanol, acetone and a butanol.

12. The process of claim 1, further comprising performing a filtration step selected from the group consisting of ultrafiltration, microfiltration, nanofiltration and reverse osmosis between steps (a) and (b).

13. The process of claim 1, wherein step (b) is carried out as pervaporation.

14. The process of claim 1, wherein step (b) is carried out using a first membrane selected from the group consisting of polymeric membranes and inorganic membranes.

15. The process of claim 1, wherein the first conditions that provide the first driving force comprise heating the first feed stream before step (b).

16. The process of claim 1, wherein the dephlegmator has a length and is further adapted to provide heat exchange between the gas stream and a coolant stream over at least a part of the length.

17. The process of claim 1, wherein the dephlegmator includes at least a section containing structured packing.

18. The process of claim 1, wherein heat energy supplied to step (c) by the first permeate stream is supplemented by heating at least a portion of the condensate stream to form a return vapor stream and returning the return vapor stream to the dephlegmator to provide supplemental heat energy.

19. The process of claim 18, wherein a total heat energy is supplied to step (c) by the first permeate stream and the return vapor stream, and wherein at least 80% of the total heat energy is supplied by the first permeate stream.

20. The process of claim 18, wherein a total heat energy is supplied to step (c) by the first permeate stream and the return vapor stream, and wherein at least 90% of the total heat energy is supplied by the first permeate stream.

21. The process of claim 1, wherein a total heat energy is supplied to step (c) and the total heat energy is supplied solely by the first permeate stream.

22. The process of claim 1, wherein the overhead stream is condensed and then heated before step (d).

23. The process of claim 1, wherein the overhead stream is compressed before step (d).

24. The process of claim 1, wherein step (d) is carried out using a second membrane selected from the group consisting of polymeric membranes and inorganic membranes.

25. The process of claim 1, wherein the condensate stream is recirculated within the process.

26. The process of claim 1, wherein the condensate stream is recirculated to step (b).

27. The process of claim 1, wherein the second permeate stream is recirculated within the process.

28. The process of claim 1, wherein the second permeate stream is recirculated to step (c).

29. The process of claim 1, wherein the first residue stream is recirculated to step (a).

30. The process of claim 1, further comprising passing the alcohol product stream to a molecular sieve and withdrawing from the molecular sieve a high-purity alcohol product stream.

31. The process of claim 1, wherein step (b) is carried out in two sub-steps.

32. The process of claim 1, wherein step (d) is carried out in two sub-steps.

33. The process of claim 1, wherein step (a) is carried out on a batch basis.

34. The process of claim 1, wherein step (a) is carried out on a continuous basis.

35. A process for producing ethanol, comprising the following steps:
(a) fermenting a sugar to form a fermentation broth comprising ethanol and water;
(b) filtering at least a portion of the fermentation broth to produce a filtrate stream;
(c) performing a first membrane separation step, comprising:
(i) providing a first membrane having a first feed side and a first permeate side;
(ii) passing the filtrate stream as a liquid feed stream across the first feed side under first conditions that provide a first driving force for transmembrane permeation;
(iii) withdrawing from the first feed side a residue stream depleted in ethanol compared with the liquid feed stream;
(iv) withdrawing from the first permeate side a first permeate stream enriched in ethanol compared with the liquid feed stream;
(d) performing a dephlegmation step, comprising:
(i) providing a dephlegmator having a coolant flow side and a gas stream flow side and adapted for partial condensation of a gas stream by providing countercurrent flow between the rising gas stream and a falling condensate stream;
(ii) passing at least a portion of the first permeate stream into the dephlegmator as the gas stream;
(iii) flowing a coolant across the coolant flow side in heat-exchanging relationship with the gas stream;
(iv) withdrawing from the dephlegmator an overhead stream enriched in ethanol compared with the gas stream;
(v) withdrawing from the dephlegmator a condensate stream depleted in ethanol compared with the gas stream;
(e) performing a second membrane separation step comprising:
(i) providing a second membrane having a second feed side and a second permeate side;
(ii) passing at least a portion of the overhead stream across the second feed side under conditions that provide a second driving force for transmembrane permeation;
(iii) withdrawing from the second feed side an ethanol product stream enriched in ethanol compared with the overhead stream;
(iv) withdrawing from the second permeate side a second permeate stream depleted in ethanol compared with the overhead stream.

36. The process of claim 35, wherein heat energy supplied to step (d) by the first permeate stream is supplemented by heating at least a portion of the condensate stream to form a return vapor stream and returning the return vapor stream to the dephlegmator.

37. The process of claim 35, wherein a total heat energy is supplied to step (d) and at least 80% of the total heat energy is supplied by the first permeate stream.

38. The process of claim 35, wherein the overhead stream is condensed and then heated before step (e).

39. The process of claim 35, wherein the overhead stream is compressed before step (e).

* * * * *